(12) United States Patent
Behnke et al.

(10) Patent No.: US 9,474,564 B2
(45) Date of Patent: *Oct. 25, 2016

(54) METHOD AND SYSTEM FOR COMPENSATING FOR EXTERNAL IMPEDANCE OF AN ENERGY CARRYING COMPONENT WHEN CONTROLLING AN ELECTROSURGICAL GENERATOR

(75) Inventors: Robert Behnke, Erie, CO (US); Robert H. Wham, Boulder, CO (US)

(73) Assignee: COVIDIEN AG, Neuhasen am Rheinfall (CH)

( * ) Notice: Subject to any disclaimer, the term of this patent is extended or adjusted under 35 U.S.C. 154(b) by 2072 days.

This patent is subject to a terminal disclaimer.

(21) Appl. No.: 11/389,956

(22) Filed: Mar. 27, 2006

(65) Prior Publication Data

US 2006/0224152 A1    Oct. 5, 2006

Related U.S. Application Data

(60) Provisional application No. 60/666,797, filed on Mar. 31, 2005.

(51) Int. Cl.
*A61B 18/12* (2006.01)
*A61B 18/00* (2006.01)

(52) U.S. Cl.
CPC .. *A61B 18/1206* (2013.01); *A61B 2018/00702* (2013.01); *A61B 2018/00755* (2013.01); *A61B 2018/00779* (2013.01); *A61B 2018/00869* (2013.01); *A61B 2018/00875* (2013.01)

(58) Field of Classification Search
CPC ............... A61B 18/1206; A61B 2018/00702; A61B 2018/00755; A61B 2018/00779; A61B 2018/00875; A61B 2018/00869

USPC ..................... 606/32, 34–25, 37–403, 34–35
See application file for complete search history.

(56) References Cited

U.S. PATENT DOCUMENTS

| 1,787,709 A | 1/1931 | Wappler |
| 1,813,902 A | 7/1931 | Bovie |

(Continued)

FOREIGN PATENT DOCUMENTS

| DE | 179607 | 3/1905 |
| DE | 1099658 | 2/1961 |

(Continued)

OTHER PUBLICATIONS

International Search Report EP 07008207.8, dated Sep. 5, 2007.

(Continued)

*Primary Examiner* — Michael Peffley
*Assistant Examiner* — Samantha Good

(57) ABSTRACT

A control system for use with an electrosurgical generator which delivers electrosurgical energy to tissue has a control module. The module includes a processor executing an algorithm. The algorithm has the steps of determining a sensed voltage value corresponding to a sensed voltage signal output by the electrosurgical generator and determining a sensed current value corresponding to a sensed current signal output by the electrosurgical generator. The algorithm has the steps of determining phase information corresponding to a phase shift between the voltage signal and the current signal and determining a characteristic related to the electrosurgical energy delivered to the tissue using the phase information, the sensed voltage value and the sensed current value.

10 Claims, 7 Drawing Sheets

(56) References Cited

U.S. PATENT DOCUMENTS

| | | |
|---|---|---|
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Humio Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |

(56) References Cited

U.S. PATENT DOCUMENTS

| | | | |
|---|---|---|---|
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A * | 12/1994 | Klicek et al. ............... 606/35 |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A * | 6/1995 | Matsunaga ............... 324/142 |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson |
| 5,438,302 A | 8/1995 | Goble |
| 5,443,463 A | 8/1995 | Stern et al. |
| 5,445,635 A * | 8/1995 | Denen et al. ............... 606/27 |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa |
| 5,540,684 A | 7/1996 | Hassler, Jr. |
| 5,541,376 A | 7/1996 | Ladtkow et al. |
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |

(56) References Cited

U.S. PATENT DOCUMENTS

| | | |
|---|---|---|
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A * | 3/2000 | Ichikawa et al. ............... 606/38 |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,093,186 A | 7/2000 | Goble |
| 6,102,497 A | 8/2000 | Ehr et al. |
| 6,102,907 A | 8/2000 | Smethers et al. |
| 6,106,524 A * | 8/2000 | Eggers et al. ................... 606/50 |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |

(56) References Cited

U.S. PATENT DOCUMENTS

| | | |
|---|---|---|
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside et al. |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |

(56) References Cited

U.S. PATENT DOCUMENTS

| | | |
|---|---|---|
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 * | 11/2007 | Wham et al. .......... 606/34 |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin |
| 2003/0004510 A1 * | 1/2003 | Wham et al. .......... 606/51 |
| 2003/0060818 A1 | 3/2003 | Kannenberg |
| 2003/0078572 A1 | 4/2003 | Pearson et al. |
| 2003/0139741 A1 | 7/2003 | Goble et al. |
| 2003/0153908 A1 | 8/2003 | Goble |
| 2003/0163123 A1 | 8/2003 | Goble |
| 2003/0163124 A1 | 8/2003 | Goble |
| 2003/0171745 A1 | 9/2003 | Francischelli |
| 2003/0181898 A1 | 9/2003 | Bowers |
| 2003/0199863 A1 | 10/2003 | Swanson |
| 2003/0225401 A1 | 12/2003 | Eggers et al. |
| 2004/0002745 A1 | 1/2004 | Fleming |
| 2004/0006337 A1 * | 1/2004 | Nasab et al. .......... 606/41 |
| 2004/0015159 A1 | 1/2004 | Slater et al. |
| 2004/0015163 A1 * | 1/2004 | Buysse et al. .......... 606/34 |
| 2004/0015216 A1 | 1/2004 | DeSisto |
| 2004/0019347 A1 | 1/2004 | Sakurai |
| 2004/0024395 A1 * | 2/2004 | Ellman et al. .......... 606/37 |
| 2004/0030328 A1 | 2/2004 | Eggers |
| 2004/0030330 A1 | 2/2004 | Brassell et al. |
| 2004/0044339 A1 | 3/2004 | Beller |
| 2004/0049179 A1 | 3/2004 | Francischelli |
| 2004/0054365 A1 | 3/2004 | Goble |
| 2004/0059323 A1 | 3/2004 | Sturm |
| 2004/0068304 A1 | 4/2004 | Paton |
| 2004/0082946 A1 | 4/2004 | Malis |
| 2004/0095100 A1 | 5/2004 | Thompson |
| 2004/0097912 A1 | 5/2004 | Gonnering |
| 2004/0097914 A1 | 5/2004 | Pantera |
| 2004/0097915 A1 | 5/2004 | Refior |
| 2004/0116919 A1 | 6/2004 | Heim |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek et al. |
| 2004/0193148 A1 | 9/2004 | Wham et al. |

(56) References Cited

U.S. PATENT DOCUMENTS

| | | |
|---|---|---|
| 2004/0230189 A1 | 11/2004 | Keppel |
| 2004/0243120 A1 | 12/2004 | Orszulak et al. |
| 2004/0260279 A1 | 12/2004 | Goble |
| 2005/0004564 A1 | 1/2005 | Wham |
| 2005/0004569 A1 | 1/2005 | Witt et al. |
| 2005/0004634 A1 | 1/2005 | Ricart et al. |
| 2005/0021020 A1 | 1/2005 | Blaha et al. |
| 2005/0021022 A1 | 1/2005 | Sturm et al. |
| 2005/0101949 A1 | 5/2005 | Harano et al. |
| 2005/0101951 A1 | 5/2005 | Wham |
| 2005/0109111 A1 | 5/2005 | Manlove et al. |
| 2005/0113818 A1 | 5/2005 | Sartor |
| 2005/0113819 A1 | 5/2005 | Wham |
| 2005/0149151 A1 | 7/2005 | Orszulak |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 A1 | 5/1995 |
| DE | 19717411 | 11/1998 |
| DE | 19848540 A1 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 4/2006 |
| EP | 0880220 B1 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |

(56) References Cited

FOREIGN PATENT DOCUMENTS

| WO | WO98/18395 | 5/1998 |
|---|---|---|
| WO | WO98/27880 | 7/1998 |
| WO | WO99/12607 | 3/1999 |
| WO | WO02/00129 | 1/2002 |
| WO | WO02/011634 | 2/2002 |
| WO | WO 02/32335 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2005/060365 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060849 | 7/2005 |
| WO | WO2006/050888 | 5/2006 |
| WO | WO2006/105121 | 10/2006 |
| WO | WO 2008/003058 | 1/2008 |

OTHER PUBLICATIONS

International Search Report EP 07010673.7 dated Sep. 24, 2007.
International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences-Yingyong Kexue Xuebao, Shanghai CN, vol. 23 No. 2;(Mar. 2005); 160-164.
International Search Report EP06022028.2.
International Search Report EP06025700.3.
International Search Report EP07001481.6.
International Search Report EP07001485.7.
International Search Report EP07001527.6.
International Search Report EP07004355.9.
Muller et al., "Extended Left Hemicolectomy Using the LigaSure Vessel Sealing System" Innovations That Work; Sep. 1999.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo at al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes at al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation—'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
International Search Report PCT/US03/37110 dated Jul. 25, 2005.
International Search Report PCT/US03/37310 dated Aug. 13, 2004.
International Search Report EP 04009964.dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
Ni W et al: "A Signal Processing Method for the Coriolis Mass Flowmeter Based on a Normalized . . . " Journal of Applied Sciences—Yingyong Kexue Xuebao, Shanghai CN, vol. 23 No. 2;(Mar. 2005); 160-164.
US 6,878,148, 4/2005, Goble et al. (withdrawn).
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
Supplementary European Search Report dated Nov. 29, 2011 for EP Appln. No. EP 09 76 3515.

* cited by examiner

METHOD AND SYSTEM FOR COMPENSATING FOR EXTERNAL IMPEDANCE OF AN ENERGY CARRYING COMPONENT WHEN CONTROLLING AN ELECTROSURGICAL GENERATOR

CROSS REFERENCE TO RELATED PATENT APPLICATIONS

The instant patent application claims priority to U.S. Provisional Patent Application Ser. No. 60/666,797 filed on Mar. 31, 2005 which is herein incorporated by reference in its entirety.

BACKGROUND

The present disclosure is directed to a control system for an electrosurgical generator, and more particularly, the present disclosure relates to an electrosurgical generator that includes a control system that compensates for the impedance of external components connected to the generator, such as a cable.

TECHNICAL FIELD

An electrosurgical generator transfers energy from the generator to a patient via cables. Surgeons control the energy application by adjusting the basic power level of the electrosurgical generator by using a hand or foot switch to control the power applied over time. However, manual control of the energy application has certain limitations, such as the overall reliability in achieving an intended power level, and other various difficulties associated with assessing and/or accessing feedback information (e.g., visual and tactile feedback), particularly during endoscopic procedures.

A circuit for automatically controlling the output of an electrosurgical generator is disclosed in U.S. Pat. No. 6,210,403 to Klicek, currently owned, and assigned to Sherwood Services AG. U.S. Pat. No. 6,210,403 relates to an electrosurgical generator control, which is responsive to the tissue impedance between active and return electrodes during desiccation.

Impedance associated with inductance, capacitance, and resistance in components through which energy flows from the generator to the patient can change the amount of actual energy delivered to the patient by the generator. For example, cables transferring electrosurgical energy generated by the generator to an electrosurgical delivery device have inductance, resistance and shunt capacitance that may affect the energy flow. A monopolar cable in which the active and return lines are separated has a small amount of capacitance but has a greater amount of inductance. A bipolar cable having the active and return lines included within the same cable has higher capacitance but a reduced inductance. Other components may introduce impedance into the energy flow, e.g., board traces, blocking capacitors and handheld electrosurgical delivery devices (e.g., electrosurgical handsets, pencils, etc.).

When tissue impedance (e.g., the impedance of the patient tissue between electrodes delivering the electrosurgical energy) is low, the generator is able to produce high current and low voltage. The inductance and resistance of the cable (and/or other components that may introduce impedance) reduces the amount of voltage delivered to the patient proportional to the amount of current delivered, i.e., as the current increases the voltage drops across the cable and/or other components. This drop makes it difficult to accurately measure the voltage at the patient end or tissue site. When tissue impedance is high, the output voltage increases, causing more current to flow through the capacitance of the cable and/or the other components. The additional current is known as leakage current. Leakage current decreases the actual current delivered to the patient. Furthermore, impedance in the cable and/or the other components interferes with accurately measuring the tissue impedance.

In addition to taking into account impedances for cables and/or the other components, phase difference between voltage and current at the output of the generator provides valuable information for accurately determining the actual electrosurgical energy being delivered to the patient. However, it is not known to use complex impedance information for the cable and/or the other components together with the voltage, current and phase information at the output of the electrosurgical generator for calculating energy loss in the cable and/or the other components and therefore actual electrosurgical energy delivered to the patient.

SUMMARY

According to one embodiment of the present disclosure, there is provided a control system associated with an electrosurgical generator generating electrosurgical energy which is delivered to a patient. The system includes a control module having at least one processor. The processor executes an algorithm having the steps of: determining at least one of a sensed voltage value corresponding to a sensed voltage signal output by the electrosurgical generator and determining a sensed current value. The sensed current value corresponds to a sensed current signal output by the electrosurgical generator. The algorithm also includes the steps of determining phase information corresponding to a phase shift between the at least one voltage signal and at least one current signal; and determining a characteristic related to the electrosurgical energy delivered to the patient using the phase information, the sensed voltage value and the sensed current value.

In another embodiment of the present disclosure, the algorithm further may include the step of sampling impedance information corresponding to impedance of at least one energy-carrying component. The characteristic step may further include using the sampled impedance information and modulating the electrosurgical energy delivered to the patient using the sampled impedance information.

The control system may obtain the phase information from circuitry selected from the group consisting of zero cross phase detector circuitry, processing circuitry and any combinations thereof. The processing circuitry may be configured to execute an algorithm selected from the group consisting of a single-band Fourier transform algorithm, a multi-band Fourier transform algorithm, an FFT algorithm, a Goertzel algorithm, an equivalent to a Fourier transform algorithm and any combinations thereof.

The impedance information may be associated with at least one parameter selected from the group consisting of an inductance of the component, a resistance of the component, a capacitance of the component, a leakage capacitance of the component and any combinations thereof. The impedance information may also be obtained by a device selected from the group consisting of a user input device, an encoded readable information associated with the at least one component, a mechanical device setting associated with the at least one component, a stored information accessible to the at least one processor and any combinations thereof.

The characteristic of the electrosurgical energy delivered to the patient may be selected from the group consisting of voltage, current, impedance and power.

In another embodiment of the present disclosure, the algorithm may include the step of: controlling at least one of voltage, current and power output by the electrosurgical generator in accordance with the determined at least one characteristic related to the delivered electrosurgical energy.

According to still another embodiment of the present disclosure, a control system may be provided with a control module including at least one processor. The processor being configured to execute an algorithm with the steps of: determining at least one of a sensed voltage value corresponding to a sensed voltage signal output by the electrosurgical generator and determining a sensed current value corresponding to a sensed current signal output by the electrosurgical generator. The algorithm also includes the steps of: determining impedance information corresponding to impedance of at least one energy carrying component; and determining at least one characteristic related to the electrosurgical energy delivered to the patient using the impedance information and at least one of the sensed voltage value and the sensed current value.

The impedance information of this embodiment may also be associated with at least one of inductance, resistance, capacitance, leakage capacitance of the at least one component and a combination thereof. Alternatively, the impedance information may be associated utilizing one of the aforementioned input devices.

Another embodiment according to the present disclosure includes a method for regulating electrosurgical energy output by an electrosurgical generator. The method includes the steps of determining a sensed voltage value corresponding to a sensed voltage signal output by the electrosurgical generator, and determining a sensed current value corresponding to a sensed current signal output by the electrosurgical generator. The method also includes the steps of: determining a phase shift value corresponding to a phase shift between the voltage signal and current signal; and determining a characteristic related to the electrosurgical energy delivered to the patient using the phase shift value and at least one of the sensed voltage value and the sensed current value. The method further has the step of: determining at least one of voltage, current and power output by the electrosurgical generator in accordance with the determined characteristic related to the delivered electrosurgical energy.

According to another aspect of the present disclosure, there is provided a method for compensating an output of an electrosurgical system for an external device of an electrosurgical system. The method includes the steps of: determining an impedance factor of the external device utilizing a first algorithm and determining a voltage factor adjacent an electrode utilizing a second algorithm. The method also has the steps of determining a current factor adjacent the electrode utilizing a third algorithm; and determining a phase parameter factor of the output utilizing a fourth algorithm and determining power lost in the external device using at least one of the impedance factor, the voltage factor, the current factor, and the phase parameter factor to obtain a difference value. The method further includes the steps of comparing the difference value to a threshold value related to the external device and modulating at least one of the power, the load, and the current depending on the relationship of the difference value to the threshold value.

The phase parameter factor of the output may be calculated by a phase differential of a voltage signal and a current signal of the output.

The phase parameter factor of the output may also be calculated by a plurality of phase differentials between successive voltage signals and current signals of the output.

The electrosurgical generator may also be configured to include a current sensor for measuring the output current delivered by the generator, a microprocessor electrically connected to the current sensor and an impedance sensor for calculating one or more parameters of an electrosurgical energy. The generator may also include an electrical conduit defined therein which has an encoded rating. The encoding rating communicates to an input of the electrosurgical generator. The encoded rating can relate to a loss of energy from the conduit. The electrosurgical generator outputs a compensated signal to attribute for the loss from the conduit. The encoded rating may optionally be displayed on an exterior of the conduit, and may be automatically or manually communicated to a receiver of the generator. Alternatively, the encoded rating is wirelessly communicated to the generator by a transmitter, a receiver or a transceiver.

BRIEF DESCRIPTION OF THE DRAWINGS

Various embodiments are described herein below with reference to the drawings wherein.

DETAILED DESCRIPTION OF THE EMBODIMENTS

Figure 1:
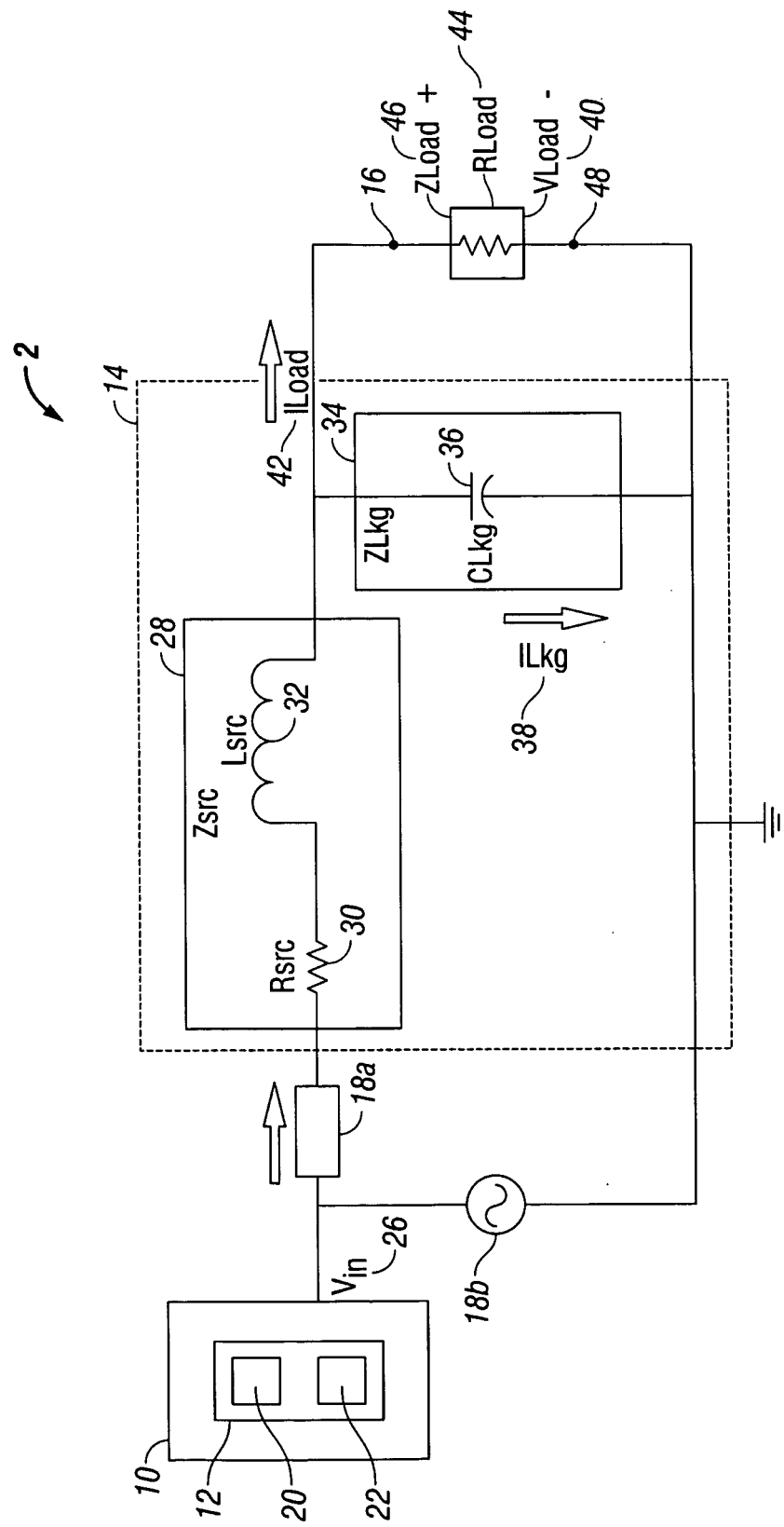
FIG. 1 is a schematic diagram of an electrosurgical system in accordance with one embodiment of the present disclosure.

Embodiments of the presently disclosed system and method are described with reference to the drawings, where like reference numerals refer to similar elements throughout the various figures. Referring to FIG. 1, there is shown an exemplary embodiment of an electrosurgical system 2 having an electrosurgical generator 10 providing electrosurgical energy to a patient, also referred to as the load. A control system 12 is provided for controlling the output of the electrosurgical generator 10. The electrosurgical generator 10 outputs energy including a voltage $V_{in}$ 26, which is transferred or carried to the patient, tissue, or destination via one or more energy carrying components, such as a cable, a blocking capacitor, a circuit board, a handset of an electrosurgical instrument, etc. The cable and/or the other components collectively have exemplary characteristics represented by box 14, which may be represented as a series inductor and shunt capacitor. A first impedance $Z_{src}$ 28 associated with box 14 includes resistance $R_{src}$ 30 and inductance $L_{src}$ 32. A second impedance $Z_{Lkg}$ 34 associated with box 14 includes capacitance $C_{Lkg}$ 36 through which a leakage current $I_{Lkg}$ 38 flows. The electrosurgical energy is delivered to the patient via at least one electrode 16 of the electrosurgical instrument. A voltage $V_{load}$ 40 and a current $I_{load}$ 42 are delivered to the patient having a load impedance $Z_{load}$ 46, which is associated with the tissue resistive load, $R_{load}$ 44.

The electrosurgical instrument may be configured in a bipolar configuration, where first electrode 16 and second electrodes 48 are both present in the electrosurgical instrument with the second electrode 48 providing the return path for the output of electrosurgical generator 10. In a monopolar configuration, the electrosurgical instrument includes the first electrode 16 while the second electrode 48 is connected to a surface near the patient and provides the return path. The active ends of first and second electrodes 16, 48 are electrically connected to electrosurgical generator 10 by one or more conductive cables. Monopolar and bipolar configurations used in electrosurgical generators are electrically equivalent and equally suited for use with control system 12 of the present disclosure.

The electrosurgical generator 10 may include a power supply (not explicitly shown) for generating energy and an output stage (not explicitly shown) for modulating the energy, such as via a waveform generator. The power supply generates energy, such as RF, microwave, ultrasound, infrared, ultraviolet, laser or thermal energy. In the exemplary embodiment, the power supply generates RF energy having a high voltage and a frequency of about 470 KHz.

The electrosurgical generator 10 and/or control system 12 may be connected, e.g., via a network, such as the internet, to a remote processor, such as, a server and/or database providing processing resources, such as, information (e.g., instrument operating information, mappings), storage, algorithms and/or programs. Updated information may be provided on a regular basis and downloaded to the generator 10 and/or control system 12 as needed and/or prior to surgery. As can be appreciated, this enables the user to obtain updated information regarding operation of the instrument, electrical parameters, patient parameters, control parameters, etc. In addition, this also enables the generator manufacturer to provide updated information on a regular basis. A user may also be able to receive diagnostics remotely in this fashion relating to the instruments and/or generators being utilized, either on demand by the user, prior to an operation, or automatically during a scheduled download.

The control system 12 may include one or more digital signal processors 20 and a control module 22 executable on the processor(s) 20. The digital processor(s) 20 and/or control module 22 may include one or more digital signal processors (DSP) and associated circuitry. The control system 12 may further include circuitry including analog, digital and/or logic devices (not explicitly shown). The DSPs may be upgradeable using flash ROM as is known in the art. Upgrades for the DSPs may be stored on computer readable media such as compact flash media, magnetic disks, optical disks, magnetic tape, or other suitable media. Furthermore, the control system 12 may reside at least partially on the remote processor. The DSPs could be replaced by any system capable of mathematic operations. In one such embodiment, the control system 12 may be a field programmable gate array.

The control module 22 includes suitable software instructions executable by the processor 20 for processing input data, and for generating control signals that are output to the electrosurgical generator 10 for regulating the electrosurgical energy output by the electrosurgical generator. The software instructions may be stored in a storage medium such as a memory internal to the processor 20 and/or a memory accessible by the processor 20, such as a disk drive, a compact flash, a wireless memory, an internal memory, an external memory, e.g., ROM, an external hard drive, floppy diskette, CD-ROM, etc. Control signals from the control module 22, which control the electrosurgical generator 10, may be converted to analog signals by a digital-to-analog converter (DAC), which may be integrated with processor 20 or external thereto.

The electrosurgical generator 10 obtains information, such as complex impedance information for the cable and/or the other suitable components ($Z_{src}$ 28 and $Z_{Lkg}$ 34), phase information related to the phase relationship between the current and voltage signals output by the electrosurgical generator, information relating to the voltage and/or current output by the electrosurgical generator 10 generated by at least one of sensors 18, digital information generated by a processing device (not shown), and/or a combination thereof. The above stated information may be provided to the control system as input data and processed by the control system 12. A portion of the input data may be entered by a user via one or more user interfaces (not explicitly shown, e.g., a knob, slider, a keypad, etc.), which may be provided, for example, on a panel of the electrosurgical generator 10.

At least a portion of the input data is provided by sensors 18, which include a voltage sensing circuit 18a and a current sensing circuit 18b for sensing the voltage and current, respectively, output by the electrosurgical generator 10. In the exemplary embodiment described, the voltage sensing circuit 18a and the current sensing circuit 18b output respective signals $V_{rms}$, $I_{rms}$, which are representative of the voltage and current sensed, respectively. The sensors 18a, 18b provide the actual current and the voltage waveforms, but the root mean squared voltage and room mean squared current are determined by the control system 12. It should be appreciated that the actual waveforms are used as the phase of the signal cannot be readily calculated from the root mean squared values $V_{rms}$, $I_{rms}$. The sensors 18a and 18b are operatively coupled to the control system 12 for providing $V_{rms}$ and $I_{rms}$ signals to the control system 12. Circuitry may be provided for interfacing between the device providing input signals (e.g., user input device, sensors 18, etc.) and the electrosurgical generator, such as for converting the input signals into a form and/or form that is compatible with the control system 12. For example, an A/D converter may be provided for converting $I_{rms}$ and $V_{rms}$ into digital signals that can be processed by the control system 12.

The phase information describes a phase difference between current and voltage waveforms output by the electrosurgical generator 10. In one embodiment of the disclosure, the phase information is provided by circuitry, such as zero cross phase detector circuitry (not explicitly shown). In another embodiment of the disclosure, the phase information is determined by the control system 12 or an external processing system by execution of a suitable software algorithm, such as a single-band Fourier transform algorithm, a multi-band Fourier transform algorithm, an FFT algorithm, a Goertzel algorithm, an equivalent to a Fourier transform algorithm or a combination thereof. U.S. patent application Ser. No. 10/719,305, which is incorporated herein by reference in its entirety, describes a control system that uses a Goertzel algorithm to determine the phase difference between the voltage waveform and the current waveform output by an electrosurgical generator. The phase difference is used to determine the output of the electrosurgical generator and compensate for energy delivery to the operating site.

Relevant information from U.S. patent application Ser. No. 10/719,305 related to an exemplary implementation of the Goertzel algorithm is described below. In an exemplary embodiment, the Goertzel algorithm is advantageously implemented as a second order recursive infinite impulse response filter, as shown below.

The Goertzel algorithm is defined by the equation:

$$Hfi(z) = \frac{1 - \frac{2\pi f_i}{e f_s z^{-1}}}{1 - 2\cos\left(\frac{2\pi f_i}{f_s}\right) z^{-1} + z^{-2}}$$

Where $f_i$ is the frequency of interest and $f_s$ the sampling frequency.

Second Order Recursive Goertzel Filter

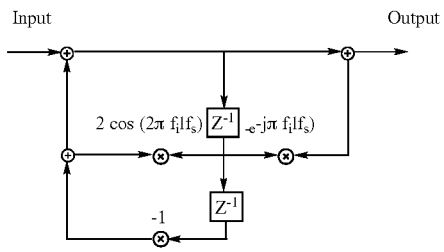

The Goertzel algorithm is implemented digitally as:

$$vk[n] = x[n] + 2\cos\left(\frac{2\pi k}{N}\right) vk[n-1] - vk[n-2]$$

where $v_k$ is the output of the filter, x is the input sample of the waveform and n is the sample number.

Since the output frequency of electrosurgical generator 10 is known, and preferably, about 470 KHz, the digitally implemented Goertzel algorithm calculates the real and imaginary frequency components of the known waveform using the following formulae:

Real=$(v_k[n-1]-(v_k[n-2]*\cos(2\pi k/N))$

Imaginary=$(v_k[n-2]*\sin(2\pi k/N))$

Magnitude=square_root(Real$^2$+Imaginary$^2$)

Phase=ATAN(Imaginary/Real)

DSPs of control module 22 calculate the voltage phase (Voltage_Phase) for a voltage signal sensed by voltage sensing circuit 18a and the current phase (Current_Phase) for a current signal sensed by current sensing circuit 18b according to the above-mentioned formulae. Calculation of Voltage_Phase and Current_Phase may be performed concurrently. Additionally, the phase shift, preferably in radians, between the voltage signal and the current signal can then be calculated by subtracting the difference in the current and voltage phases as follows:

VIPhase=Current_Phase−Voltage_Phase.

This phase calculation is implemented to calculate the phase differential between the voltage signal and the current signal. In an embodiment, the DSPs of control module 22 include (e.g., store and/or execute) the Goertzel algorithm along with associated processing software to determine the phase difference VIPhase between the voltage signal and the current signal. Additionally, control module 22 may determine a magnitude value of both the voltage and current signals according to the magnitude formula provided above.

The impedance information, e.g., $Z_{src}$ 28 and $Z_{Lkg}$ 34, are represented in rectangular form. Zsrc 28 includes impedance related to inductance $L_{src}$ 32 and resistance $R_{src}$ 30 associated with the cable and/or the other suitable components. $Z_{Lkg}$ 34 includes impedance related to capacitance $C_{Lkg}$ 36 within the cable and/or the other components, such as leakage capacitance between active and return lines of the cable. $Z_{src}$ 28 and $Z_{Lkg}$ 34 may be provided as configuration file parameters to the control system 12, such as by hard coding them into the system software of the control system 12, or inputting them to the control module 22 either automatically or by a user. For example, $Z_{src}$ 28 and $Z_{Lkg}$ 34 may be read directly from the cable and/or the other components by way of reading in (e.g., sensing, scanning and/or decoding) an encoding provided in association with or actually affixed to or embedded in the cable and/or the other component itself (e.g., a bar code, an optical reader, a radiofrequency identification or RFID tag, a transmitted code, a resistor arrangement, a color code, resistance, capacitance, mechanical pin setting, etc.). A computer readable storage medium (e.g., a ROM associated with a handset, a smart card and/or a user insertable memory) may be provided in association with the cable and/or the other components for storing information related thereto, including $Z_{src}$ 28 and/or $Z_{Lkg}$ 34. Thus, the control module 22 is capable of compensating for many different types of cable and other suitable components. The components for reading in the encoded impedance information may be included with the control system 12 or external thereto.

In one embodiment, the control module 22 performs the following algorithm for determining the current, voltage and power output by the electrosurgical generator 10 to compensate for the impedance in the cable and/or the other components as represented in FIG. 1. A different circuit configuration may be used other than the configuration shown in FIG. 1, and the algorithm performed may be different to correlate with the different circuit configuration.

Assuming a sinusoidal structure regardless of the actual waveform, the $V_{rms}$ and $I_{rms}$ values are converted to complex polar (phasor) form of magnitude ($V_{mag}$ and $I_{mag}$) and phase (in radians) (e.g., $V_{phase}$ and $I_{phase}$), where $VI_{Phase}$ is the phase shift between the voltage and current waveforms in radians. $VI_{Phase}$ may be obtained, for example, by an algorithm using the Goertzel filter, as described above, where the phase shift of $V_{in}$ 26 is assumed to be 0.

The algorithm proceeds as follows:

$V\text{mag}:=V{rms}\cdot\sqrt{2}$ $V_{phase}:=0$ $$I\text{mag}:=I rms\cdot\sqrt{2}$$

$$I\text{phase}:=VI\text{phase}$$

The polar form values are then converted to rectangular form complex numbers as follows, where $V_{sen}$ and $I_{sen}$ are the values from the voltage sensor 18a and current sensor 18b in complex rectangular form, respectively:

$$V\text{sen}:=V\text{mag}+0\cdot 1i$$

$$I\text{sen}:=I\text{mag}\cdot\cos(VI\text{phase})+I\text{mag}\cdot\sin(VI\text{phase})\cdot 1i$$

Using complex math, the following calculations for determining $V_{load}$ and $V_{load\_rms}$ are performed:

$$V\text{load}:=V\text{sen}-I\text{sen}\cdot Z src$$

The algorithm converts back to RMS using the magnitude of $V_{load\ as}$ follows:

$$V\text{load\_rms} = |V load| \cdot \frac{1}{\sqrt{2}}$$

Using the complex math, the following calculations for $I_{lkg}$ 38, $I_{load}$ 42 and $I_{load\_rms}$ are performed:

$$Ilkg := \frac{Vload}{Zlkg}$$

$$Iload: = Isen - Ilkg$$

The algorithm converts back to RMS using the magnitude of Iload as follows:

$$I\text{load\_rms} = |Iload| \cdot \frac{1}{\sqrt{2}}$$

$R_{load}$ 44 is calculated as the magnitude of the complex ratio of $V_{load}$ 40 and $I_{load}$ 42 as follows:

$$Rload: = \left|\frac{Vload}{Iload}\right|$$

The average power delivered to the load is calculated, given that:

$$P\text{avg\_load}:=V\text{load\_rms}\cdot I\text{load\_rms}\cdot\cos(\varphi)$$

and $$P\text{avg\_load}:=RE(V\text{load}\cdot\overline{I\text{load}});$$

where $V_{load}$ 40 and $I_{load}$ 42 for the above equation are complex RMS phasors and $\overline{Iload}$ is the complex conjugate of $I_{load}$ 42.

The algorithm converts $V_{load}$ 40 and $I_{load}$ 42 to the RMS phasor as follows:

$$P\text{avg\_load} = RE\left(\frac{Vload}{\sqrt{2}} \cdot \frac{\overline{Iload}}{\sqrt{2}}\right)$$

$P_{avg\_Load}$ as calculated above may be used to adjust the power to the load. Alternatively, the $P_{avg}$ calculated from the V*I samples may be used, where $P_{avg}$ represents the average power delivered to the entire network.

With reference to FIGS. 2-7, the improvement in accuracy by utilizing characteristics related to electrosurgical energy delivered to a patient using phase information is demonstrated by performing calculations that would be performed by the control module 22 using exemplary input parameters, including phase information. The characteristics determined include at least power, voltage, current and impedance at the load. The results are compared to results from calculations that do not use phase information to actual measured values. Furthermore, it is shown that the use of phase information correctly compensates for measuring on a generator side of a blocking cap of an electrosurgical generator system.

The following equations are used to determine the transfer function of box 14 show in FIG. 1, where the input parameters are defined as follows:

Vin frequency is:

$$f_o:=470 \text{ KHz}$$

The jω term for the reactance is:

$$s:=2\cdot\pi\cdot i\cdot f_o$$

Cable and/or other component inductance is:

$$L_o:=2\times 10^{-6}\cdot H$$

Cable Capacitance (usually is equal to around 200 pF, but is exaggerated here for illustrative purposes and clarity):

$$C_o:=600 \text{ pF}$$

Cable resistance:

$$R_w:=7\Omega$$

Blocking capacitor:

$$C_b:=47000 \text{ pF}$$

Arbitrary input voltage:

$$V_{in}:=150V$$

The below equations are for equivalent capacitor resistance and equivalent inductance resistance of the cable, etc., without using phase information, but using magnitude values.

Equivalent Capacitor Resistance:

$$X_c := \left|\frac{1}{s\cdot C_o}\right| \qquad X_c: = 564.379\ \Omega$$

Equivalent Blocking Capacitor Resistance:

$$X_{cb} := \left|\frac{1}{s\cdot C_b}\right| \qquad X_{cb}: = 7.205\ \Omega$$

Equivalent Inductance Resistance Added with the Wire Resistance:

$$X_1:=|s\cdot L_o|+R_w$$

$$X_1:=6.606\Omega$$

A range of load impedance is set from 1 to 1 kΩ:

$$R_o:=1\Omega,2\Omega\ldots 1000\Omega$$

Voltage at the Load:

The actual voltage at the load is calculated, where $R_{eq}$ combines the load impedance with the cable capacitance, which are shown in FIG. 1 to be parallel. By using the s parameter in the equation, the phase information is kept in tact.

$$R_{eq}(R_o) := \frac{R_o \cdot \frac{1}{s \cdot C_o}}{R_o + \frac{1}{s \cdot C_o}}$$

The transfer function for the resonating circuit, including the blocking capacitor is as follows:

$$V_o(R_{eq}) := \frac{V_{in} \cdot R_{eq}}{R_{eq} + s \cdot L_o + R_w + \frac{1}{s \cdot C_b}}$$

$I_{in}$, the signal off the sensors with phase information is calculated as follows:

$$I_{in}(R_{eq}) := \frac{V_{in}}{R_{eq} + s \cdot L_o + R_w + \frac{1}{s \cdot C_b}}$$

The above equation shows all the variables involved with measuring current $I_{in}$, the measurement from the current sensing circuit 18b, measured in rectangular format. In reality only the magnitude of the current and the phase angle between the voltage and current is measured, where the measurements would be provided in polar form $I\angle\phi$, which would need to be converted to rectangular coordinates for the following equation:

$$V_{src\_cmplx}(I_{in}) := I_{in} \cdot \left(s \cdot L_0 + R_w + \frac{1}{s \cdot C_b}\right)$$

Without considering phase information for the voltage at the load, the magnitude of the voltage delivered to the load is:

$$V_1(V_{src\_cmplx}) := |V_{in} - V_{src\_cmplx}|$$

Figure 2:
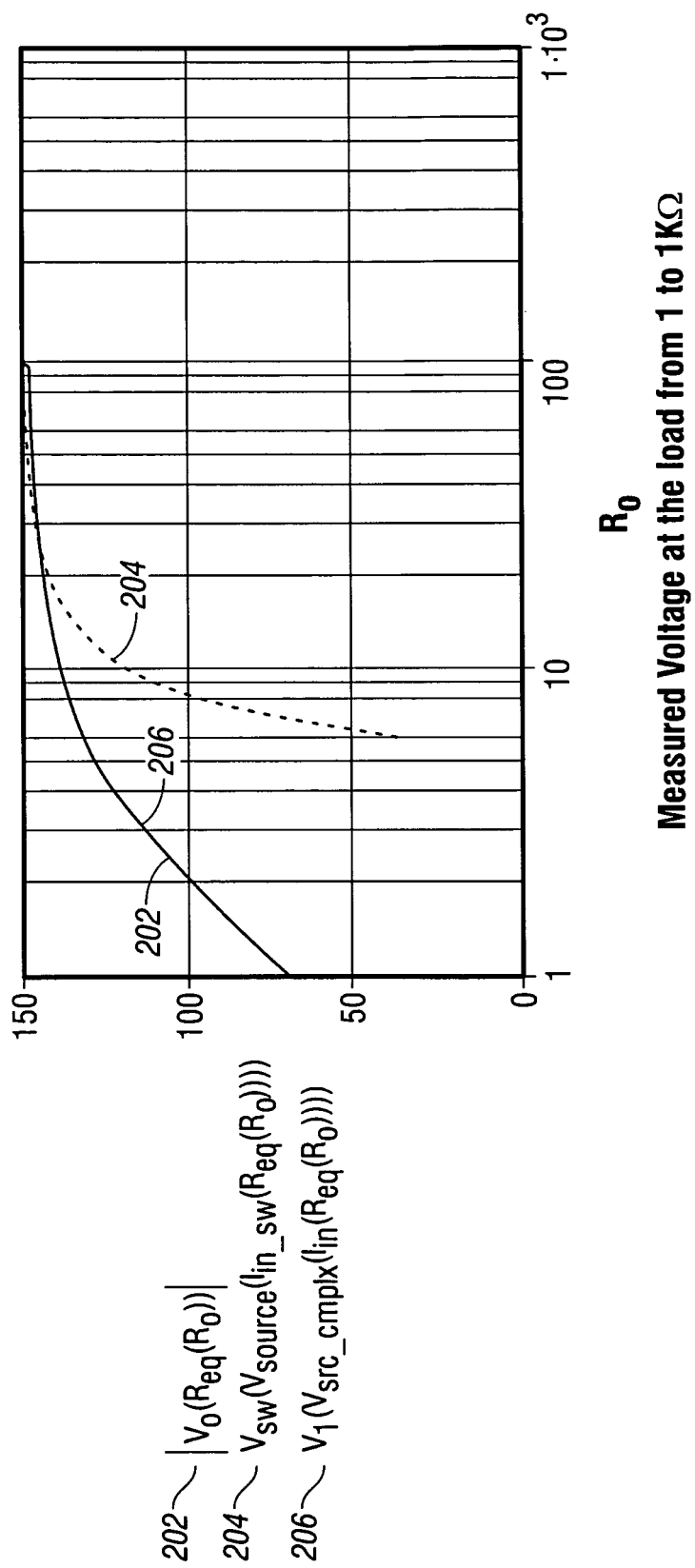
FIG. 2 is a plot of a voltage at a load to which electrosurgical energy is applied compared to calculated voltage at the load, including calculations performed using a control system of the electrosurgical system shown in FIG. 1.

With respect to FIG. 2, trace 202 shows voltages at the load ($V_o$), trace 204 shows calculated voltages at the load without using phase information ($V_{sw}$), and trace 206 shows calculated voltages at the load ($V_l$) using phase information. Traces 206 coincides with trace 202 throughout the range shown, while trace 204 is significantly displaced from trace 202 for the range 1Ω-20Ω, indicating that below 20Ω the voltage is not accurately calculated without using phase information, and that the calculations using the phase information accurately measure the voltage at the load.

Current at the Load:

In this example, the actual current at the load is calculated by dividing the actual calculated voltage at the load ($V_o$) and dividing it by the impedance at the load as follows:

$$I_o(V_o, R_o) := \frac{V_o}{R_o}$$

The leakage current is calculated using the phase information as follows:

$$I_{lkg\_cmplx}(V_1) := \frac{V_1}{\frac{1}{s \cdot C_o}}$$

The sensor measurement is used with the phase information as follows:

$$I_l(I_{lkg\_cmplx}, I_{in}) := |I_{in} - I_{lkg\_cmplx}|$$

With respect to FIG. 3, a range of interest is set for the load impedance ranging from 1 kΩ to 10 kΩ, where $R_o := 1000, 1001 \ldots 10000$ Trace 302 corresponds to the load current as follows:

$$I_{out}(R_o) := I_o(V_o(R_{eq}(R_o)), R_o)$$

Trace 304 corresponds to calculation of the load current without phase information:

$$I_{sw\_out}(R_o) := I_{sw}(I_{in\_sw}(R_{eq}(R_o)), I_{lkg}(V_{sw}(V_{source}(I_{in\_sw}R_{eq}(R_o))))))$$

Trace 306 corresponds to calculations for the load current phase information:

$$I_{load}(R_o) := I_l(I_{lkg\_cmplx}(V_1(V_{src\_cmplx}(I_{in}(R_{eq}(R_o))))), I_{in}(R_{eq}(R_o)))$$

Figure 3:
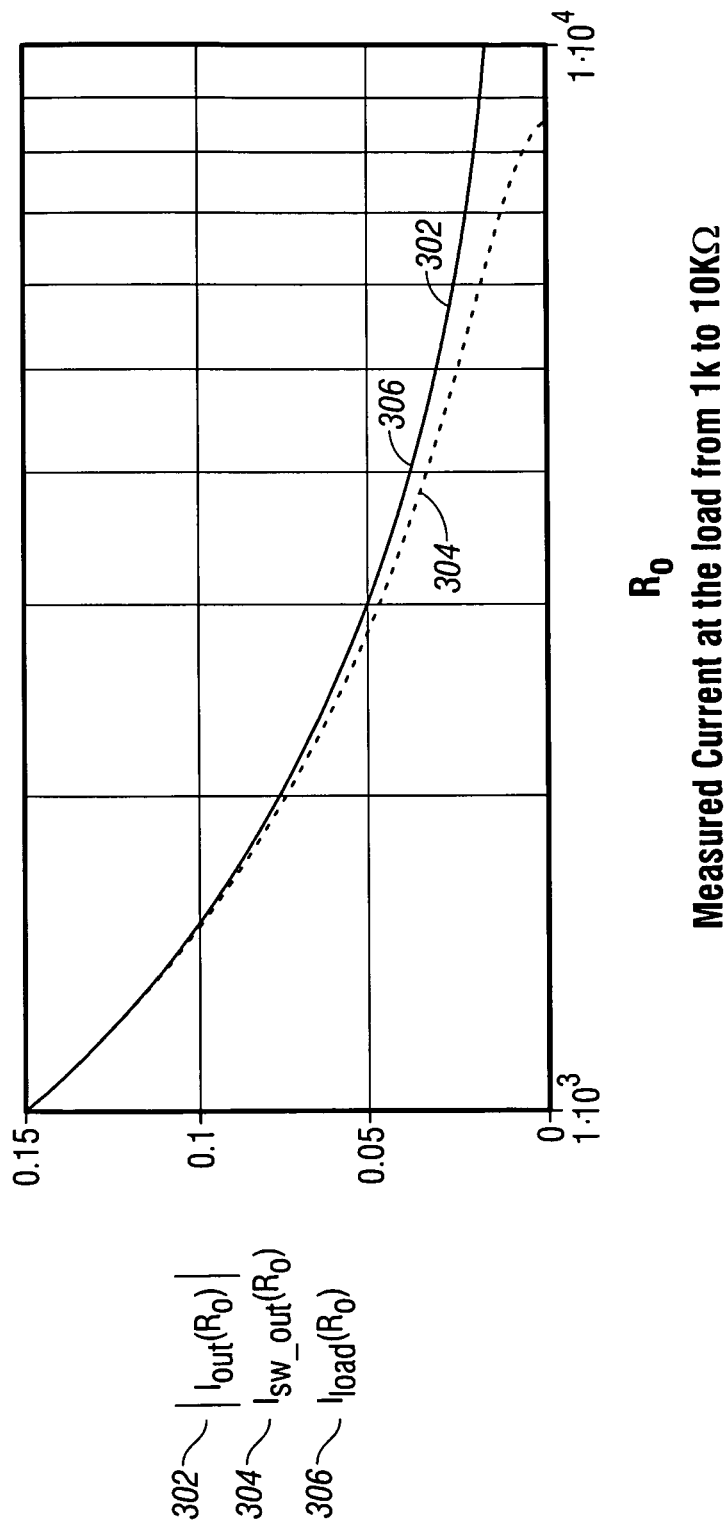
FIG. 3 is a plot of a current at a load to which electrosurgical energy is applied compared to calculated current at the load, including calculations performed using a control system of the electrosurgical system shown in FIG. 1.

As shown in FIG. 3, trace 306 substantially coincides with trace 302 throughout the range shown indicating that the calculations using the phase information accurately measure the current at the load, while trace 304 lags below trace 302 for load impedance values 2 kΩ or above. The differential between traces 304 and 302 would increase if the output voltage were to be increased.

Impedance at the Load:

The actual load impedance is $R_o$.

The load impedance with the phase information is calculated as follows:

$$R_l(V_l, I_l) := \frac{V_l}{I_l}$$

Since the measured load voltage is off at the low impedance and the measured current is off at the high impedance, the load range is split into two sections.

Figure 4:
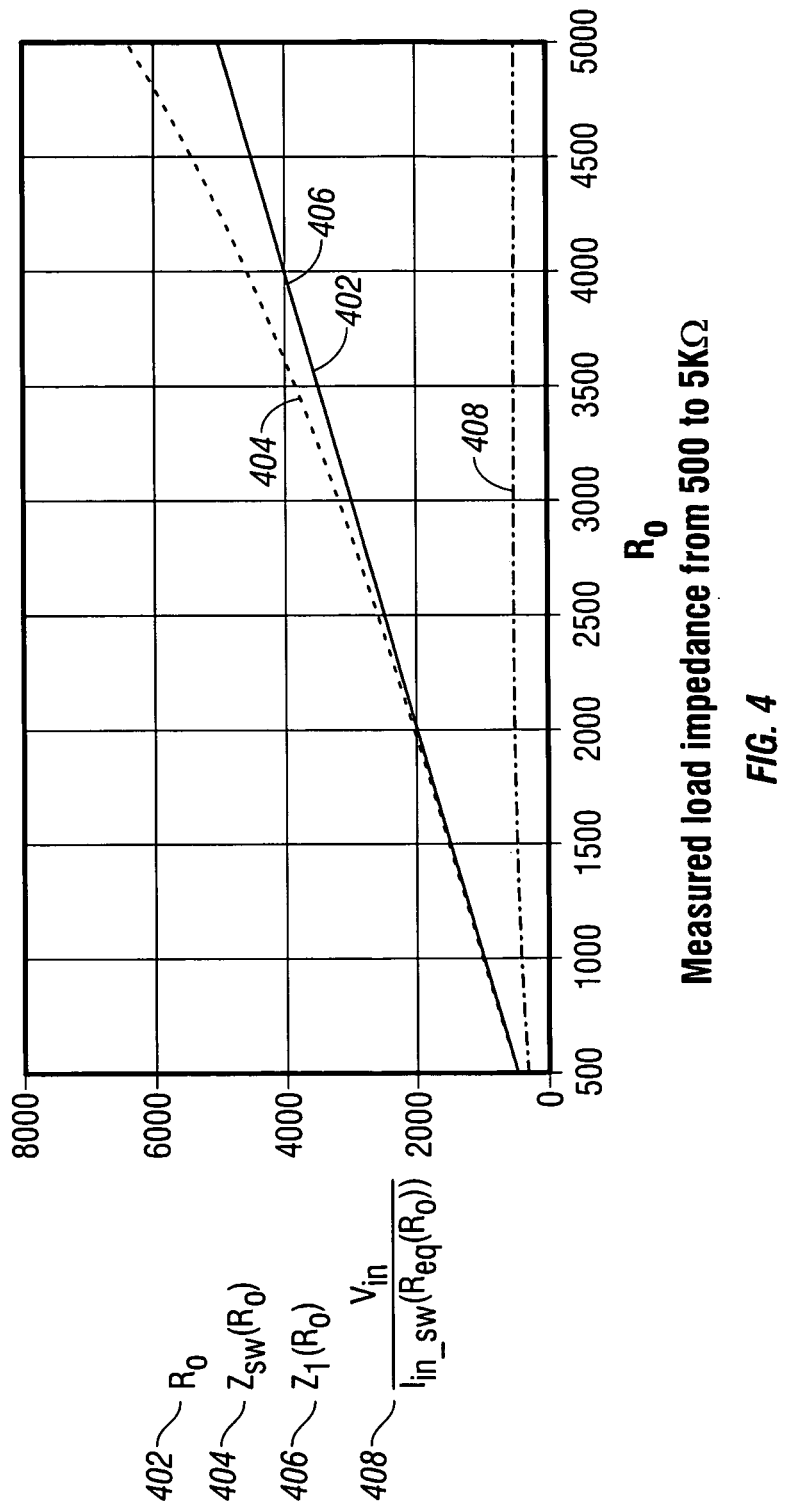
FIG. 4 is a plot for a high end of impedance of load impedance at a load to which electrosurgical energy is applied compared to calculated load impedance at the load, including calculations performed using a control system of the electrosurgical system shown in FIG. 1.

FIG. 4 shows the high end of impedance:

Trace 402 corresponds to the load impedance as follows:

$$R_o := 500, 501 \ldots 5000$$

Trace 404 corresponds to calculation and compensation for the load impedance without phase information as follows:

$$Z_{sw}(R_o) := R_{sw}(V_{sw}(V_{source}(I_{in\_sw}(R_{eq}(R_o)))), I_{sw}(I_{in\_sw}R_{eq}(R_o)), I_{lkg}(V_{sw}(V_{source}(I_{in\_sw}(R_{eq}(R_o)))))))$$

Trace 406 corresponds to calculation and compensation for the load impedance with phase information as follows:

$$Z_l(R_o) := R_l(V_l(V_{src\_cmplx}(I_{in}(R_{eq}(R_o)))), I_l(I_{lkg\_cmplx}(V_1(V_{src\_cmplx}(V_1(V_{src\_complx}(I_{in}(R_{eq}(R_o))))))), I_{in}(R_{eq}(R_o))))$$

Trace 408 corresponds to calculation for load impedance without compensation.

Trace 404 is significantly displaces from trace 402. Trace 406 substantially coincides with trace 402, indicating accurate calculation and compensation of the load impedance. Trace 408 stays at around 500Ω due to the equivalent capacitor resistance of the cable.

Figure 5:
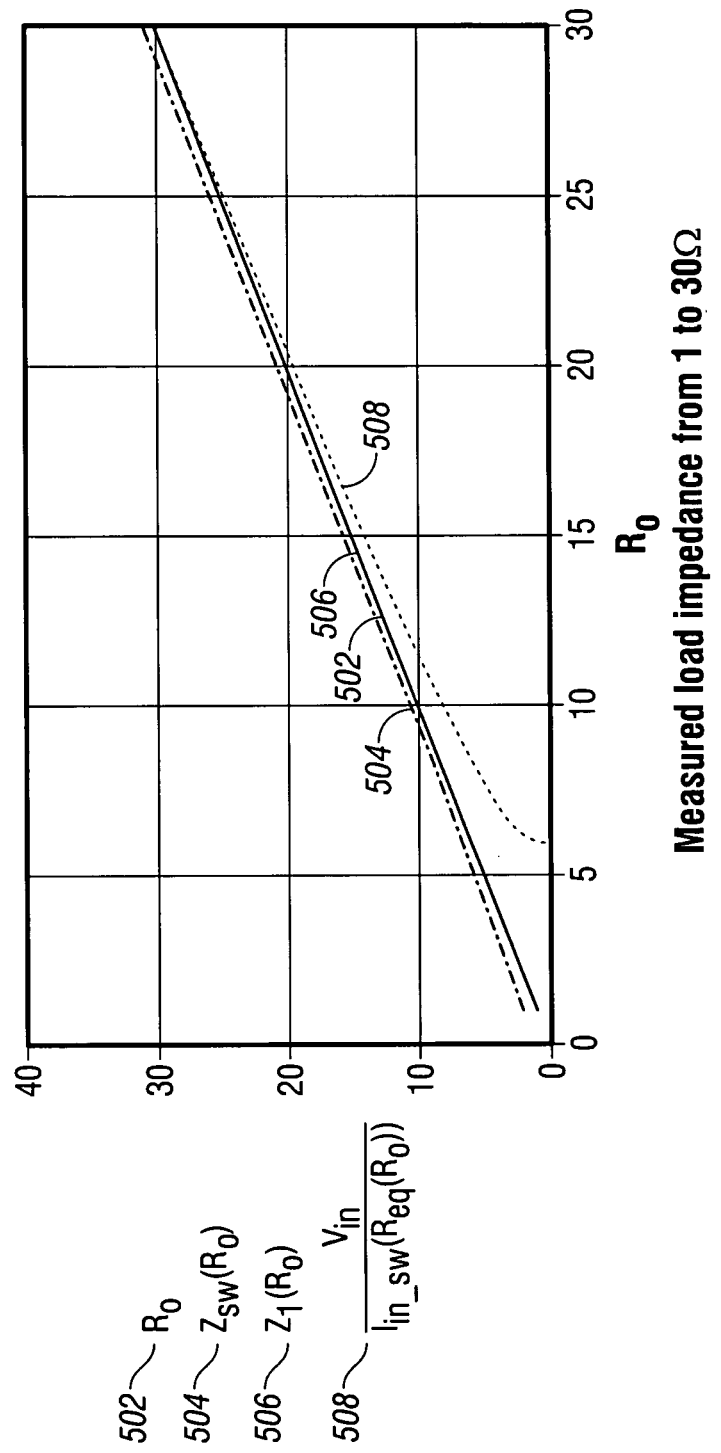
FIG. 5 is a plot for a low end of impedance of load impedance at a load to which electrosurgical energy is applied compared to calculated load impedance at the load, including calculations performed using a control system of the electrosurgical system shown in FIG. 1.

FIG. 5 shows the low end of impedance:

Trace 502 corresponds to the load impedance as follows:

$$R_o := 1, 1.1 \ldots 30$$

Similar to trace 404, trace 504 corresponds to calculation and compensation of the load impedance without phase information as follows:

$$Z_{sw}(R_o) := R_{sw}(V_{sw}(V_{source}(I_{in\_sw}(R_{eq}(R_o)))), I_{sw}(I_{in\_sw}(R_{eq}(R_o))), I_{lkg}(V_{sw}(V_{source}(I_{in\_sw}(R_{eq}(R_o)))))))$$

Similar to trace 404, trace 506 corresponds to calculation and compensation of the load impedance with phase information as follows:

$$Z_l(R_o) := R_l(V_l(V_{src\_cmplx}(I_{in}(R_{eq}(R_o)))), I_l(I_{lkg\_cmplx}(V_l(V_{src\_cmplx}(I_{in}(R_{eq}(R_o)))), I_{in}(R_{eq}(R_o)))))$$

Similar to trace 408, trace 508 corresponds to calculations for load impedance without compensation as follows.

Trace 504 is significantly displaces from trace 502. Trace 506 substantially coincides with trace 402, indicating accurate calculation and compensation of the load impedance. Trace 508 stays at around 500Ω due to the equivalent capacitor resistance of the cable.

While only the range 1-30Ω is shown, trace 504 is accurate for the range 20 to 2000Ω; however, below 20 ohms trace 504 is displaced from trace 502. Trace 508 shows the impedance calculation with no correction performed. Trace 508 is close to the load impedance between 0 and 400Ω. Trace 506 coincides with trace 502 for the entire range, indicating accurate calculation and compensation of the load impedance.

Power at the Load:

The actual power at the load is:

$$P_o(V_o, R_o) := \left| \frac{V_o^2}{R_o} \right|$$

The power at the load with phase information is calculated as follows:

$$P_l(V_l, I_l) := V_l \cdot I_l$$

The power at the load without any correction is calculated as follows:

$$P_{uc}(I_{in\_sw}) := V_{in} \cdot I_{in\_sw}$$

Figure 6:
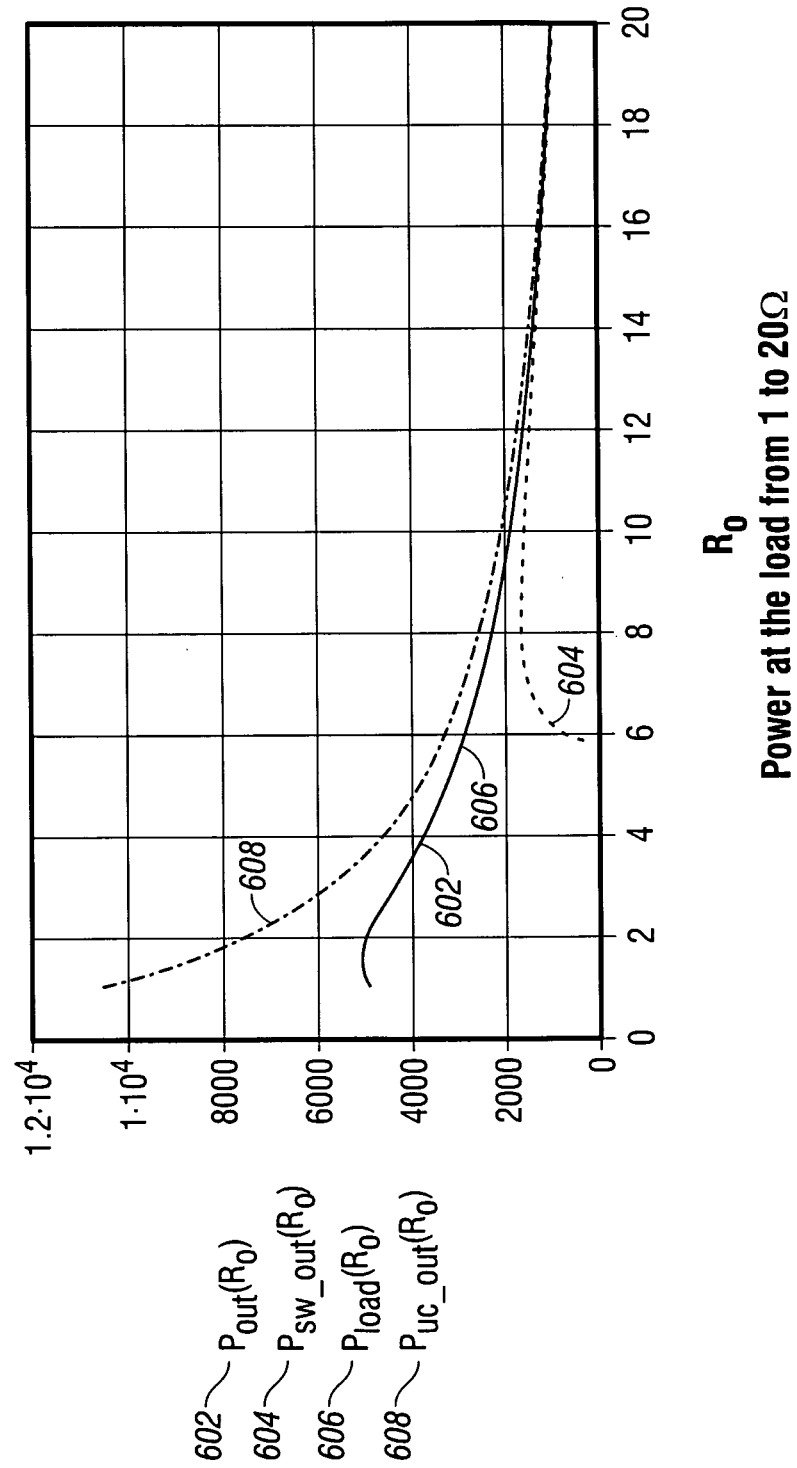
FIG. 6 is a plot for a low end of impedance of power at a load to which electrosurgical energy is applied compared to calculated power at the load, including calculations performed using a control system of the electrosurgical system shown in FIG. 1.

With respect to FIG. 6, power at the load for a low impedance range is shown, where $$R_o := 1, 1.1 \ldots 20$$

Figure 7:
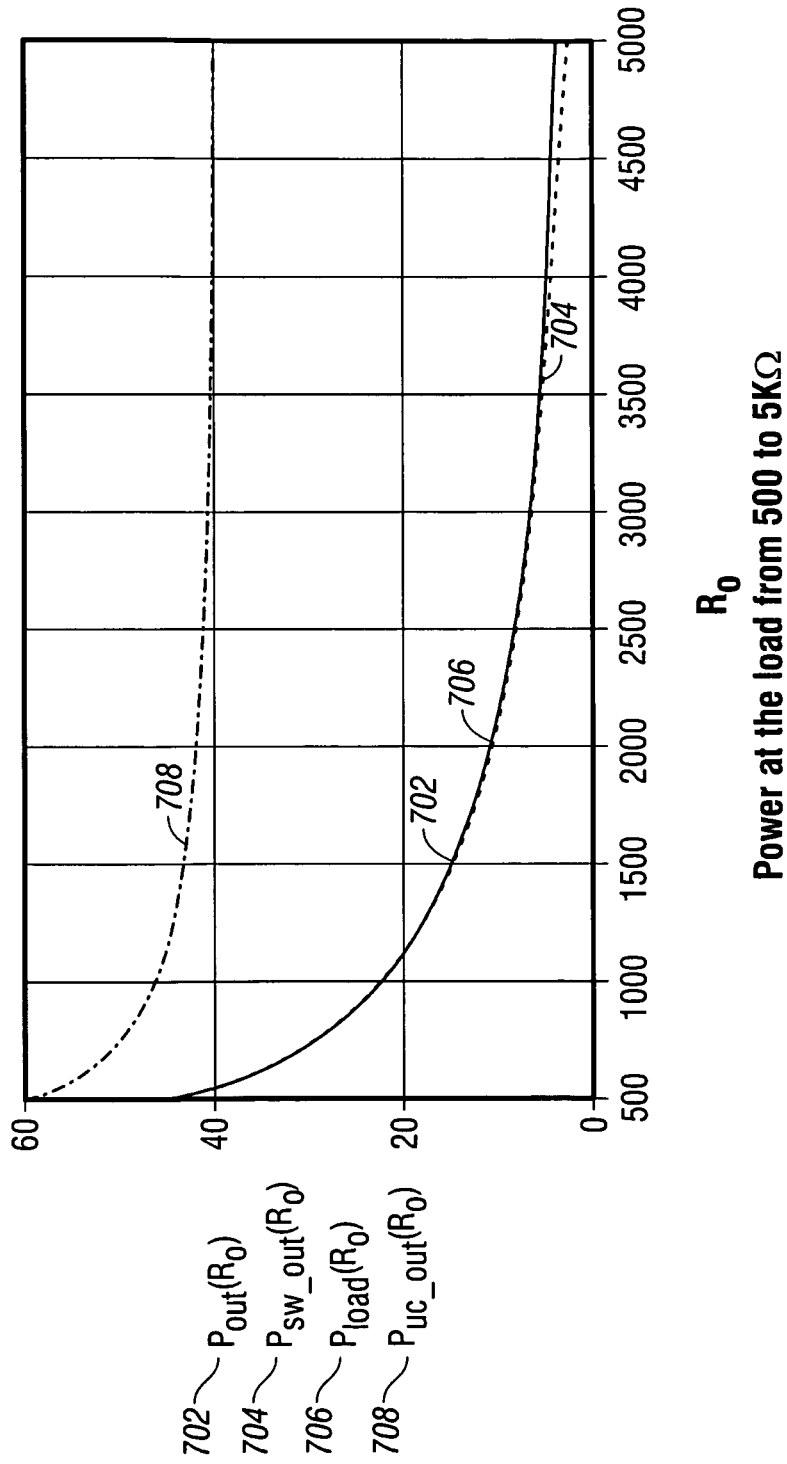
FIG. 7 is a plot for a high end of impedance of power at a load to which electrosurgical energy is applied compared to calculated power at the load, including calculations performed using a control system of the electrosurgical system shown in FIG. 1.

With respect to FIG. 7, power at the load for a high impedance range is shown, where $$R_o := 500, 501 \ldots 5000$$

Traces 602 and 702 correspond to the following $$P_{out}(R_o) := P_o(V_o(R_{eq}(R_o)), R_o)$$

Traces 604 and 704 correspond to the following:

$$P_{sw\_out}(R_o) := P_{sw}(V_{sw}(V_{source}(I_{in\_sw}(R_{eq}(R_o)))), I_{sw}(I_{in\_sw}(R_{eq}(R_o))), I_{lkg}(V_{sw}(V_{source}(I_{in\_sw}(R_{eq}(R_o))))))$$

Traces 606 and 706 correspond to the following:

$$P_{load}(R_o) := P_l(V_l(V_{src\_cmplx}(I_{in}(R_{eq}(R_o)))), I_l(I_{lkg\_cmplx}(V_l(V_{src\_cmplx}(I_{in}(R_{eq}(R_o)))), I_{in}(R_{eq}(R_o)))))$$

Traces 608 and 708 correspond to the following:

$$P_{uc\_out}(R_o) := P_{uc}(I_{in\_sw}(R_{eq}(R_o)))$$

Trace 606 coincides with trace 602, and trace 706 coincides with trace 702, indicating accurate calculation and compensation of the power at the load. Accuracy of calculations for power at the load without compensation is degraded for impedances that are below 10 ohms and above 200 ohms. Accuracy of calculations for power at the load with compensation but without phase information is degraded for impedances that are below 15 ohms and above 3000 ohms. Using phase information would correct the calculations for power at the load across the entire impedance range.

Errors in compensation for voltage and current at the load are compounded when calculating impedance and power at the load. Provision of phase information in addition to impedance information for the cable and/or the other components contributes to accurate measurement and calculation of parameters of the energy delivered at the load.

Advantageously, the use of the phase difference information and/or the complex impedance information for the cable and/or the other components maximizes accuracy for determining characteristics related to energy delivered to the patient because the present disclosure compensates for the radiofrequency energy lost in the energy-carrying component, and delivers another amount of accurate radiofrequency energy to the patient to attribute for the energy loss. Accurate determination of characteristics related to delivered energy may be used, for example, to track energy delivery and/or tissue effect, compensate for energy losses for providing energy having desired characteristics (current, voltage, power, etc.) to the patient, etc. Furthermore, the use of the phase difference information and/or the complex impedance information advantageously contributes to obtaining an accurate measurement of the patient impedance ($Z_{load}$, which is substantially equivalent to $Rl_{oad}$), which may be altered due to factors, such as impedance of the cable and/or the other components.

Although this disclosure has been described with respect to particular embodiments, it will be readily apparent to those having ordinary skill in the art to which it appertains that changes and modifications may be made thereto without departing from the spirit or scope of the disclosure. While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of particular embodiments.

What is claimed is:

1. An electrosurgical system comprising:
    an electrosurgical generator for delivering electrosurgical energy to tissue;
    a surgical instrument connected to the electrosurgical generator; and
    a control module including at least one processor, said at least one processor executing an algorithm comprising the steps of:
        determining at least one of a sensed voltage value corresponding to a sensed voltage signal output by the electrosurgical generator;
        determining a sensed current value corresponding to a sensed current signal output by the electrosurgical generator;

determining complex impedance information corresponding to impedance of each cable of a plurality of cables connecting the electrosurgical generator to the surgical instrument; and determining at least one characteristic related to the electrosurgical energy delivered to a patient by using the complex impedance information corresponding to the impedance of each of the cables of the plurality of cables connecting the electrosurgical generator to the surgical instrument;

wherein the control module compensates for the electrosurgical energy lost in each of the cables of the plurality of cables by altering an amount of the electrosurgical energy delivered to tissue of the patient in accordance with (i) the complex impedance information corresponding to the impedance of each of the cables of the plurality of cables connecting the generator to the surgical instrument and (ii) updated information periodically provided in a wireless manner from a network to the electrosurgical generator and the control module, the updated information including at least electrical parameters, patient parameters, control parameters, and diagnostics relating to the electrosurgical generator and the surgical instrument; and wherein the updated information is periodically provided on demand, before an operation performed via the surgical instrument connected to the electrosurgical generator, or automatically during predetermined time periods.

2. The electrosurgical system according to claim 1, wherein the complex impedance information relates to at least one of inductance, resistance, capacitance, leakage capacitance of each of the cables of the plurality of cables connecting the electrosurgical generator to the surgical instrument and any combination thereof.

3. The electrosurgical system according to claim 1, wherein the complex impedance information is obtained via at least one of a user input device, an encoded information associated with each of the cables of the plurality of cables, a mechanical device setting associated with each of the cables of the plurality of cables, a stored information accessible to the at least one processor, and any combinations thereof.

4. The electrosurgical system according to claim 1, wherein the at least one characteristic of the electrosurgical energy delivered to the patient is selected from the group consisting of voltage, current, impedance and power.

5. The electrosurgical system according to claim 4, wherein the algorithm further comprises the step of:
controlling at least one of voltage, current and power output by the electrosurgical generator in accordance with the determined characteristic related to the delivered electrosurgical energy.

6. A method for compensating an output of an electrosurgical system, the method comprising the steps of:
calculating a complex impedance factor corresponding to impedance of each cable of a plurality of cables connecting an electrosurgical generator to a surgical instrument by utilizing a first algorithm;
calculating a voltage factor adjacent an electrode utilizing a second algorithm;
calculating a current factor adjacent said electrode utilizing a third algorithm;
calculating a phase parameter factor of the output utilizing a fourth algorithm;
calculating power lost in each of the cables of the plurality of cables connecting the electrosurgical generator to the surgical instrument by using at least one of the complex impedance factor, the voltage factor, the current factor, and the phase parameter factor;
comparing the calculated power lost to a threshold value related to each of the cables of the plurality of cables;
modulating the power dependent on the relationship of the calculated power lost value to the threshold value; and
altering an amount of RF energy delivered to tissue of a patient in accordance with (i) the complex impedance factor corresponding to impedance of each of the cables of the plurality of cables connecting the electrosurgical generator to the surgical instrument and (ii) updated information periodically provided in a wireless manner from a network to the electrosurgical generator, the updated information including at least electrical parameters, patient parameters, control parameters, and diagnostics relating to the electrosurgical generator and the surgical instrument;
wherein the updated information is periodically provided on demand, before an operation performed via the surgical instrument connected to the electrosurgical generator, or automatically during predetermined time periods.

7. The method of claim 6, wherein the step of calculating the phase parameter factor of the output includes the step of:
calculating a phase differential of a voltage signal and a current signal of the output.

8. The method of claim 7, wherein the step of calculating the phase parameter factor of the output includes the step of:
calculating a plurality of phase differentials between successive voltage signals and current signals of the output.

9. An electrosurgical system comprising:
an electrosurgical generator configured to deliver electrosurgical energy;
an electrosurgical treatment tool adapted to connect to the electrosurgical generator, said electrosurgical treatment tool including at least one electrode and an impedance sensor;
a current sensor which measures the output current delivered by the electrosurgical generator, said electrosurgical generator including:
a microprocessor electrically connected to the current sensor and the impedance sensor which calculates complex impedance information corresponding to impedance of each cable of a plurality of cables connecting the electrosurgical generator to the electrosurgical treatment tool;
each of the cables of the plurality of cables including an encoded rating stored in a storage medium that is configured to communicate the encoded rating to an input of the electrosurgical generator, said encoded rating relating to a loss of electrosurgical energy from each of the cables of the plurality of cables; and
wherein the electrosurgical generator outputs a compensated signal attributable to the electrosurgical energy loss from each of the cables of the plurality of cables by altering an amount of the electrosurgical energy delivered to tissue of a patient in accordance with (i) the complex impedance information corresponding to the impedance of each of the cables of the plurality of cables connecting the electrosurgical generator to the electrosurgical treatment tool and (ii) updated information periodically provided in a wireless manner from a network to the electrosurgical generator, the updated information including at least electrical parameters, patient parameters, control parameters, and diagnostics relating to the electrosurgical generator and the electrosurgical treatment tool; and wherein the updated information is periodically provided on demand, before an operation performed via the electrosurgical treatment tool connected to the electrosurgical generator, or automatically during predetermined time periods.

10. The electrosurgical system of claim 9, wherein said encoded rating is automatically or visually communicated to the electrosurgical generator.

* * * * *